(12) United States Patent
Cockrem et al.

(10) Patent No.: US 6,984,293 B2
(45) Date of Patent: *Jan. 10, 2006

(54) AZEOTROPIC DISTILLATION OF CYCLIC ESTERS OF HYDROXY ORGANIC ACIDS

(76) Inventors: Michael Charles Milner Cockrem, 224 Westmorland Blvd., Madison, WI (US) 53705; Istvan Kovacs, 7545 Tree La. #208G, Madison, WI (US) 53717

( * ) Notice: Subject to any disclaimer, the term of this patent is extended or adjusted under 35 U.S.C. 154(b) by 572 days.

This patent is subject to a terminal disclaimer.

(21) Appl. No.: 09/809,534

(22) Filed: Mar. 15, 2001

(65) Prior Publication Data

US 2002/0157937 A1  Oct. 31, 2002

(51) Int. Cl.
*C07D 319/00* (2006.01)
*B01D 3/38* (2006.01)

(52) U.S. Cl. .............................. 203/14; 203/29; 203/68; 203/69; 203/70; 203/77; 203/89; 203/91; 562/589; 549/274

(58) Field of Classification Search .................. 203/14, 203/63, 68–70, 89, 77, 80, 29, 38, 43, 48, 203/59, 72, 87, 88, DIG. 6, DIG. 11, 91; 562/580, 589; 210/634; 549/274, 379, 267
See application file for complete search history.

(56) References Cited

U.S. PATENT DOCUMENTS

| | | | | |
|---|---|---|---|---|
| 321,925 A | | 7/1885 | Waite ............................ | 203/95 |
| 2,953,503 A | | 9/1960 | Freure .......................... | 202/42 |
| 3,419,478 A | * | 12/1968 | Izard ............................ | 203/70 |
| 3,432,401 A | * | 3/1969 | Tcherkawsky ................ | 203/15 |
| 3,718,545 A | * | 2/1973 | Horlenko ...................... | 203/15 |
| 4,100,189 A | | 7/1978 | Mercier ........................ | 260/541 |
| 4,136,098 A | * | 1/1979 | Burzin et al. ................. | 549/267 |
| 4,191,616 A | * | 3/1980 | Baker ........................... | 203/44 |
| 4,275,234 A | | 6/1981 | Baniel et al. ................. | 562/584 |
| 5,068,418 A | * | 11/1991 | Kulprathipanja et al. .... | 562/580 |
| 5,136,057 A | | 8/1992 | Bhatia .......................... | 549/274 |
| 5,138,074 A | | 8/1992 | Bellis et al. .................. | 549/274 |
| 5,142,023 A | | 8/1992 | Gruber et al. ................ | 528/354 |
| 5,149,833 A | | 9/1992 | Hess et al. .................... | 549/274 |
| 5,175,369 A | * | 12/1992 | Fowlkes ....................... | 564/497 |
| 5,274,073 A | | 12/1993 | Gruber et al. ................ | 528/354 |
| 5,319,107 A | | 6/1994 | Benecke et al. .............. | 549/274 |
| 5,502,215 A | | 3/1996 | Yamaguchi et al. .......... | 549/274 |
| 5,510,526 A | * | 4/1996 | Baniel et al. ................. | 562/580 |

(Continued)

FOREIGN PATENT DOCUMENTS

WO    WO98/24777    6/1998

(Continued)

OTHER PUBLICATIONS

Perry et al, Chemical Engineers' Handbook, 1950, fifth ed., see pp. 13-36 to 13-42.*

(Continued)

*Primary Examiner*—Virginia Manoharan
(74) *Attorney, Agent, or Firm*—Williams, Morgan & Amerson, P.C.

(57) ABSTRACT

Cyclic esters of hydroxy organic acids can be produced and recovered via azeotropic distillation. In certain embodiments cyclic esters, such as glycolide and lactide, can be produced from a fermentation broth or other feed stream that contains a hydroxy organic acid, an ammonium salt of a hydroxy organic acid, an amide of a hydroxy organic acid, or an ester of a hydroxy organic acid using azeotropic distillation. The hydroxy organic acid of the feed stream or the hydroxy organic acid derived from the feed stream by decomposition is reacted to produce the cyclic ester. In other embodiments a crude composition of a cyclic ester of an organic ester can be purified using azeotropic distillation.

53 Claims, 1 Drawing Sheet

U.S. PATENT DOCUMENTS

| | | | |
|---|---|---|---|
| 5,521,278 A | 5/1996 | O'Brien et al. | 528/354 |
| 5,750,732 A | 5/1998 | Verser et al. | 549/274 |
| 5,780,678 A | 7/1998 | Baniel et al. | 562/580 |
| 5,831,122 A | 11/1998 | Eyal | 562/580 |
| 5,959,144 A | 9/1999 | Baniel | 562/580 |
| 6,087,532 A | 7/2000 | Baniel et al. | 562/580 |
| 6,153,708 A | 11/2000 | Aizawa et al. | 525/420 |
| 6,160,173 A | 12/2000 | Eyal et al. | 562/589 |
| 6,187,951 B1 | 2/2001 | Baniel et al. | 562/580 |

FOREIGN PATENT DOCUMENTS

| | | |
|---|---|---|
| WO | WO98/55442 | 12/1998 |
| WO | WO99/19290 | 4/1999 |
| WO | WO00/64850 | 11/2000 |

OTHER PUBLICATIONS

Perry, "Azeotropic Distillation"; *Chemical Engineers' Handbook, Fifth Edition*, 13:36-42, 1973.

Holten, "Lactic acid; properties and chemistry of lactic acid and derivates", pp. 20-21, p. 36-37, and p. 425, 1971.

CRC Handbook of Chemistry and Physics, pps. D1-D33, 1981-1982.

Co-pending U.S. Appl. No. 09/809,649; Entitled: "Azeotropic Distillation Process for Producing Organic Acids or Organic Acid Amides"; filed: Mar. 15, 2001.

Co-pending U.S. Appl. No. 09/809,243; Entitled: "Process for Obtaining an Organic Acid from an Organic Acid Ammonium Salt, an Organic Acid Amide, or an Alkylamine-Organic Acid Complex"; filed: Mar. 15, 2001.

PCT/US02/06923 International Search Report (Mar. 10, 2003).

EP Application No. 02778185.5 Supplementary European Search Report (Aug. 12, 2004).

* cited by examiner

Figure 1.

AZEOTROPIC DISTILLATION OF CYCLIC ESTERS OF HYDROXY ORGANIC ACIDS

BACKGROUND OF THE INVENTION

1. Field of the Invention

The present invention relates generally to processes for both producing and recovering cyclic esters of hydroxy organic acids, such as lactic acid, glycolic acid, and lactones. More particularly, it concerns methods that use azeotropic distillation for production and recovery of such cyclic esters. It also relates to methods of forming lactide directly from crude fermentation broth containing significant water without a prior dehydration step.

2. Description of Related Art

Cyclic esters of hydroxy organic acids have a number of commercial uses. Cyclic esters such as gamma-butyrolactone are widely used as a feedstock for manufacture of various polymers. Lactide is an important compound as an intermediate for the production of polylactic acid (PLA) plastics which can be biodegraded. Similarly, glycolide can be used in the production of biodegradable polyglycolide plastics (PGA plastics).

Although PLA and PGA polymers have been known for more than half a century, they have recently been attracting much attention, primarily because of their biodegradability. PLA plastics are, for example, being used in packaging, paper coatings, absorbable surgical sutures, vessel implants, and orthopedic pins, among others. PLA and PGA plastics are attractive not only because they biodegrade into carbon dioxide and water, but also because they can be derived from renewable agricultural resources, such as corn or sugar beets. Such polymers can, in certain cases, also be produced using solvent-free processes, which can be more environmentally friendly than certain solvent-based processes used in producing plastics from petrochemicals. In addition, advances in technology are now making it possible to produce these plastics more cheaply, so that they can be produced at a price that is more competitive with plastics produced from petrochemicals. Thus, new and improved sources for biodegradable plastics are highly desirable.

High molecular weight polylactic acid (PLA plastic) can be obtained by the ring-opening polymerization of lactide. Both the chemical purity and the optical purity of lactide (there are different optical isomers of lactic acid and consequently different lactide isomers) used to produce polylactic acid can dramatically affect the nature of the polylactic acid produced from the lactide. Chemical impurities can also diminish the usefulness of lactide when it is a food additive, because impurities can, in certain instances, cause off tastes or cause the acidity of a preserved food to be modified in undesirable ways.

Polyglycolide plastics are produced by a ring-opening polymerization of glycolide, similar to production of polylactic acid polymers from lactide. The properties of the PGA plastics produced from glycolide are dependent on the quality and purity of the substrate.

Lactide is typically produced from lactic acid, and glycolide from glycolic acid. Lactide can be formed from two molecules of lactic acid, with the loss of two molecules of water. Lactide is typically formed either by "ring closing" or from a larger oligomer. In ring closing, a lactic acid dimer eliminates water to form lactide, which is a cyclic diester. In this case, the mechanism is an esterification reaction. Alternatively, the lactide can be formed from a longer oligomer of lactic acid containing, for example, 10 to 20 lactic acid molecules linked together by ester linkages as a short polymer. Elimination of two lactic acid moieties from this chain gives lactide. Such a reaction is a transesterification reaction. Alternatively, lactide can be produced by first forming an ester of lactoyl lactic acid linear dimer with some other species, such as an ethylene glycol-ether. Lactide is then formed by a transesterification reaction with elimination of the lactic acid dimer unit.

Although lactic and glycolic acids can be prepared by chemical synthesis, it is generally more cost efficient to produce such organic acids through fermentation of sugars, starch, or cheese whey, using microorganisms such as *Lactobacillus delbrueckii*. Such microorganisms convert monosaccharides such as glucose, fructose, or galactose, or disaccharides such as sucrose, maltose, or lactose, into such organic acids. The broth that results from fermentation contains unfermented sugars, carbohydrates, amino acids, proteins, and salts, as well as the desired acids. Some of these materials can interfere with downstream processing of an organic acid, for example processing of lactic acid to form lactide. The organic acid usually therefore must first be recovered from the fermentation broth and in some cases must undergo further purification before it can be used to produce cyclic esters.

Lactic acid or other hydroxyacids or diacids can be converted to polyesters. These polyesters can be recycled via digestion using pressurized water, acid, base, or a combination of such treatments. The products of such digestion can be a mixture of organic acids, salts of organic acids, amides of organic acids. Additionally, during processing of ammonium salts of lactic acid, there is a tendency for lactamide to form via the following reaction Lactic acid+ammonia→lactamide+water Such organic acid amides can be formed in fermentation broths.

Extraction can be used to aid in the recovery of organic acids from fermentation broths or other streams comprising organic acids and their salts (e.g., hydrolyzed polylactide, among others). Certain extractants or extraction enhancing agents can react with the hydroxy organic acid present in a feed stream to produce an ester of the hydroxy organic acid. Methods for producing lactide from sources comprising an ester of the hydroxy organic acid, hydroxy organic acid amides or ammonium salts of hydroxy organic acids are desirable.

As noted above, a typical process for the production of lactide involves the dehydration of a lactic acid stream to form a mixture of oligomers of lactic acid. This lactic acid stream can be the product of a fermentation or it can be derived from a chemical synthesis, and it is preferred that the lactic acid stream is at least partially purified before the dehydration step. After the dehydration step, the mixture of oligomers of lactic acid molecules is mixed with a depolymerization catalyst. The mixture is heated so that the lactic acid oligomers undergo thermal decomposition and cyclization (through a condensation reaction), thus producing lactide. This lactide is simultaneously or sequentially separated, often as a vapor stream. In such processes, the vapor can further comprise such impurities as monomer, dimer, and low molecular weight lactic acid oligomers, and water. When the lactide is produced from lactic acid that is the product of fermentation, the vapor can further comprise impurities derived from the fermentation, like sugars, amino acids, fatty acids, and organic acids other than lactic acid. The vapor comprising lactide can be optionally partially or fully condensed and then distilled or otherwise purified such as by fractional crystallization to form a "purified" lactide. Glycolide can be formed using similar methods.

In methods known in the art for the production of L-lactide from L-lactic acid, species such as L-lactide, meso-lactide, water, lactic acid, lactic acid linear dimer, lactic acid oligomers, lactic acid degradation products, other impurities, and traces of D-lactide can be present in varying concentrations. Thus, methods for producing relatively pure lactide, particularly optically pure lactide, are desirable. While glycolide and certain other cyclic esters of hydroxy organic acids do not have optical isomers, it is also desirable to have alternative methods for their production and purification. Thus, there is a long standing need for improved processes for the production and recovery of relatively pure lactide and glycolide and related cyclic esters. Particularly, processes that can produce cyclic esters of certain hydroxy organic acids, such as lactic acid and glycolic acid, in good purity directly from wet crude fermentation broth are desirable.

SUMMARY OF THE INVENTION

The present invention is directed to the production and the recovery of cyclic organic esters of certain hydroxy organic acids.

A "cyclic ester" produced and/or recovered in the present invention can comprise two organic acid moieties, such as lactide which is formed from two lactic acid molecules. Alternatively, a "cyclic ester" can have a single organic acid moiety, such as beta-propiolactone, which is formed from 3-hydroxypropionic acid; or such as gamma-butyrolactone, which is formed from 4-hydroxybutyric acid.

Certain cyclic esters recovered and/or produced using the present invention exist as different isomers. For example, lactide has different isomers, which have distinct physical properties. L-lactide has a melting point of 92° C. to 94° C. and is also called (3S)-cis-3,6-dimethyl-1,4-dioxane-2,5-dione. L-lactide can be formed, for example, from two L-lactic acid molecules. Meso-lactide has a melting point of 116° C. to 119° C. It is also called 3,6-dimethyl-1,4-dioxane-2,5-dione. Meso-lactide can be formed, for example, from one L-lactic acid and one D-lactic acid molecule.

DL-lactide is also called racemic lactide and can be formed by physically mixing D-lactide and L-lactide that have been separately synthesized and purified.

One embodiment of the present invention is directed to a process for the production of at least one cyclic ester of a hydroxy organic acid from a feed stream comprising at least one of a hydroxy organic acid (e.g., glycolic acid, L-lactic acid, D-lactic acid, DL-lactic acid, 4-hydroxybutyric acid, 3-hydroxypropionic acid), an ammonium salt of a hydroxy organic acid, an ester of a hydroxy organic acid, or an amide of a hydroxy organic acid. The process can be performed in either batch or continuous mode. The hydroxy organic acid of the amide, ester, ammonium salt or free acid that is a component of the feed stream can be an alpha, beta, delta, gamma, or epsilon hydroxy organic acid and preferably has from 2 to 6 carbon atoms. The feed stream can be a fermentation broth or can be derived from other sources. When the feed stream comprises an ammonium salt, a hydroxy organic acid amide, or an ester of a hydroxy organic acid a product of a thermal decomposition of the salt or the ester can be reacted to produce the cyclic ester of the hydroxy organic acid.

The process involves mixing a feed stream and at least one azeotroping agent, wherein the feed stream comprises at least one of a hydroxy organic acid, an ammonium salt of a hydroxy organic acid, an amide of a hydroxy organic acid, or an ester of a hydroxy organic acid. The azeotroping agent may be introduced as either a liquid or a vapor. The azeotroping agent is capable of forming at least one azeotrope comprising a cyclic ester of a hydroxy organic acid. Preferably the azeotroping agent is a hydrocarbon, more preferably, the hydrocarbon is greater than about 99% free of other hydrocarbons. The cyclic ester of a hydroxy organic acid is produced from a hydroxy organic acid that was originally present in the feed stream and/or that was produced by decomposition of at least one of an ammonium salt of a hydroxy organic acid, an amide of a hydroxy organic acid, or an ester of a hydroxy organic acid that was originally present in the feed stream.

Upon heating the mixture comprising the feed stream and the at least one azeotroping agent, a cyclic ester of the hydroxy organic acid is formed and a first vapor stream is produced. Alternatively, the feed stream, the azeotroping agent, or both can be heated prior to their being mixed in order to attain the temperature necessary for the production of the cyclic ester and the first vapor stream. In embodiments requiring decomposition of at least one of an ammonium salt of a hydroxy organic acid, an amide of a hydroxy organic acid, or an ester of a hydroxy organic acid present in the feed stream, the heating must also be sufficient to result in the decomposition. The first vapor stream comprises at least one azeotrope comprising the cyclic ester of the hydroxy organic acid formed by the mixing and heating of the feed stream and the azeotroping agent. Additional purification steps can be performed on the first vapor stream (e.g., condensing and crystallizing). In certain embodiments, the first vapor stream can be separated into a second vapor stream that comprises water and the azeotroping agent and a first product stream comprising the cyclic ester of the hydroxy acid and azeotroping agent. The first vapor stream can, in certain embodiments, further comprise at least one other azeotrope comprising the hydroxy organic acid and the azeotroping agent. When the first vapor stream comprises an azeotrope comprising the hydroxy organic acid, the hydroxy organic acid of the first vapor stream can subsequently be reacted to produce additional cyclic ester of the hydroxy acid and water. Optionally, a second vapor stream that comprises water and azeotroping agent can be separated from the first vapor stream producing a first product stream comprising the cyclic ester of the hydroxy acid.

In another embodiment, the present invention is directed to a process for recovering a cyclic ester of a hydroxy organic acid from a crude composition of a cyclic ester. In this process a crude composition of a cyclic ester of a hydroxy organic acid is mixed with an azeotroping agent that is capable of forming an azeotrope with the cyclic ester, and the mixture is heated to produce a vapor stream that comprises the azeotrope. The crude composition can comprise a hydroxy organic acid that the azeotroping agent is unable to form an azeotrope with, and in certain cases the hydroxy organic acid can be a precursor that can be reacted to form the cyclic ester. The vapor stream comprising the cyclic ester is condensed, and purified cyclic ester of the hydroxy organic acid can be recovered.

Yet another embodiment of the present invention is directed to a process for the production of at least one cyclic ester of a hydroxy organic acid from a feed stream comprising at least one of a hydroxy organic acid, an ammonium salt of a hydroxy organic acid, an amide of a hydroxy organic acid, or an ester of a hydroxy organic acid. The process involves mixing a feed stream and an azeotroping agent, wherein the feed stream comprises at least one of a hydroxy organic acid, an ammonium salt of a hydroxy organic acid, an amide of a hydroxy organic acid, or an ester of a hydroxy organic acid. The azeotroping agent is capable of forming at least two azeotropes: (1) a first azeotrope comprising a hydroxy organic acid and (2) a second azeotrope comprising a cyclic ester of a hydroxy organic acid. Heating the mixture comprising the feed stream and the at least one azeotroping agent can occur in a first column, and results in the production of a first vapor stream. When the feed stream comprises at least one of an ammonium salt of a hydroxy organic acid, an amide of a hydroxy organic acid, or an ester of a hydroxy organic acid, it is preferable that the heating be sufficient to cause at least some thermal decomposition of the ammonium salt, the amide, or the ester of the hydroxy organic acid to produce free hydroxy organic acid. The first vapor stream comprises a first azeotrope comprising the hydroxy organic acid and the azeotroping agent. The hydroxy organic acid of the first azeotrope can be from hydroxy organic acid originally present in the feed stream and/or from the hydroxy organic acid that is the product of thermal decomposition of at least one of an ammonium salt of a hydroxy organic acid, an amide of a hydroxy organic acid, or an ester of a hydroxy organic acid that was present in the feed stream. In certain embodiments, the first vapor stream can further comprise a second azeotrope comprising the cyclic ester. This first vapor stream is fed to a second column, wherein the hydroxy organic acid of the first vapor stream is reacted to produce a cyclic ester of the hydroxy acid and water. A second overhead vapor stream from the second column comprises water and the azeotroping agent, and a bottoms stream from the second column comprises the cyclic ester of the hydroxy acid. The cyclic ester in the bottoms stream can be the product of cyclic ester formation in the second column and in certain embodiments can also be cyclic ester from the first vapor stream.

Still another embodiment is directed to a process for the separation of a hydroxy organic acid from a cyclic ester thereof. A feed stream comprising a hydroxy organic acid and a cyclic ester thereof is mixed with at least one azeotroping agent that is capable of forming at least two azeotropes, a first azeotrope comprising the hydroxy organic acid and a second azeotrope comprising a cyclic ester of the hydroxy organic acid. Either the feed stream, the azeotroping agent, or the mixture of the two is heated to produce a first vapor stream that comprises a first azeotrope comprising the hydroxy organic acid and the azeotroping agent. The first vapor stream is separated from the mixture producing a bottoms stream comprising the cyclic ester of the hydroxy organic acid and the azeotroping agent.

In another embodiment of the invention, the azeotroping agent is capable of forming at least one azeotrope with the cyclic organic ester, but the not with the organic acid from which the ester is formed. This is the case for species such as gamma-butyrolactone formed from 4-hydroxybutyric acid and certain azeotroping agents that will distill the cyclic ester (e.g., gamma-butyrolactone) as an azeotrope but not the hydroxy acid.

In another embodiment of the invention, different isomers of a cyclic organic ester can be separated from each other by heterogeneous azeotropic distillation, such as L-lactide being separated from meso-lactide.

One advantage of this invention is that relatively low temperatures can be used in producing cyclic esters of hydroxy organic acids, for example lactide can be formed at between about 155° C. to 160° C. Another advantage of the present invention is that certain cyclic esters, such as lactide, can be formed in the presence of water without an initial dehydration of the feed stream. The ability to operate at lower temperatures decreases the rate and extent of racemization.

Additionally, no added catalyst is necessary in certain embodiments, however, a catalyst can be added to increase the rate of formation of certain cyclic esters, like lactide. Such a catalyst can be homogeneous in the liquid phase, such as tin octanoate or other soluble tin salts, but is can also be added to the liquid phase as a heterogeneous solid, or it can be present in the vapor phase as a solid catalyst. Furthermore, the soluble catalyst in the liquid phase is preferably soluble in the azeotroping agent, such as in the use of a long chain tin salt such as tin dodecanoate, or more preferably it is soluble in the organic acid phase such as in a concentrated or dilute solution of organic acid. Examples of catalysts include tin salts, hafnium salts, and other salts.

In certain preferred embodiments, the feed stream is treated to have low levels of cations of alkali metals (especially lithium, sodium, potassium), alkaline metals (especially magnesium and calcium), and lower transition metals (especially iron, nickel, zinc, and manganese) to limit racemization of optically active species. The monovalent, divalent and trivalent cations in the feed stream are removed to a large extent and replaced with the hydronium (H+) ion in this treatment. This cation exchange preferably is performed using a solid or liquid ion exchanger primarily in the hydrogen form. One example of such a solid ion exchange resin is the Amberlite IR-120H+ resin (Rohm and Haas).

The invention can be operated at atmospheric pressure in certain embodiments (e.g., about 12.7 to about 16.7 psia). At this pressure, the temperature for example for the lactide/lactic acid/dodecane system is in the vicinity of about 200° C. to 215° C., depending on concentrations of the various components.

In one embodiment, wherein the cyclic ester is formed, water is the leaving group. In this case the reaction is an esterification. In another embodiment, the leaving group can be an alcohol such as methanol. In this case, the reaction is a transesterification. In yet another embodiment, the leaving group can be ammonia or a dimer or an oligomer of the organic acid.

Thus, certain processes of the present invention can be used to produce cyclic esters, such as lactide and glycolide, in good purity via heterogeneous azeotropic distillation directly from wet crude fermentation broth that comprises hydroxy organic acid. Other embodiments of the present invention can be used to produce purified cyclic esters from crude compositions of a cyclic ester of hydroxy organic acid prepared by methods known in the art.

DESCRIPTION OF ILLUSTRATIVE EMBODIMENTS

The following definitions are used in this patent. "Lactic acid" refers to the monomeric free lactic acid as is commonly found is dilute aqueous solutions. "88% lactic acid" and "lactic acid of commerce" refer to a typical commercially available lactic acid, which is actually a mixture of monomeric lactic acid, linear dimer lactic acid or lactoyl lactic acid, short chain lactic acid oligomers, water, and also a small quantity of cyclic dimer lactic acid or lactide. When this lactic acid is diluted in a large excess of water, it will slowly hydrolyze or convert to all monomeric form lactic acid. When concentrated lactic acid is diluted with water to a 50 wt % concentration, it will slowly hydrolyze to a mixture that is largely monomeric lactic acid, but which can still contain about 3 to 4 wt % dimer lactic acid, and trace amounts of higher oligomers.

"Azeotrope" and "azeotropic" are used herein to refer to systems that contain true azeotropic mixtures as well as those that are substantially azeotropic in nature (e.g., wherein the weight percentage of each component in the mixture in the liquid phase differs from the weight percentage of that same component in the vapor phase by no more than about 5 wt %, preferably by no more than about 2 wt %, more preferably by no more than about 1 wt %).

A "heteroazeotrope" is an azeotrope that comprises more than one liquid phase.

A "binary heteroazeotrope" is an azeotrope that comprises more than one liquid phase and involves primarily two species of chemical compounds.

The "optical purity" of a cyclic ester is defined as the molar ratio of one optical isomer to the total level of all isomers. For species that form oligomers and short and long chain polymers, the optical purity can be measured and expressed on a basis after the oligomers and polymers have been converted to monomers.

A "racemic mixture" is defined as an equal mixture of D and L optical isomers of a chemical compound.

"Distillation" is defined here to mean either multistage distillation or rectification, either continuous or batch wise, as well as single stage distillation and condensation, continuous or batch wise. Multistage distillation can involve the use of reflux to increase the purity of the overhead stream and use of a reboiler or introduction of hot vapors to the bottom of the column to increase the purity of the bottoms stream, as distinguished from a single stage distillation or simple evaporation.

"Decomposition" as used herein refers to a process that results in the production of a hydroxy organic acid from an ammonium salt of a hydroxy organic acid, an amide of a hydroxy organic acid, or an ester of a hydroxy organic acid. Decomposition of an ammonium salt of a hydroxy organic acid, for example, results in the production of ammonia and the hydroxy organic acid.

"Diethylbenzene" herein refers to either mixed isomers (1,4-diethylbenzene, 1,3-diethylbenzene, and 1,2-diethylbenzene) or a single pure diethylbenzene isomer.

Figure 1:
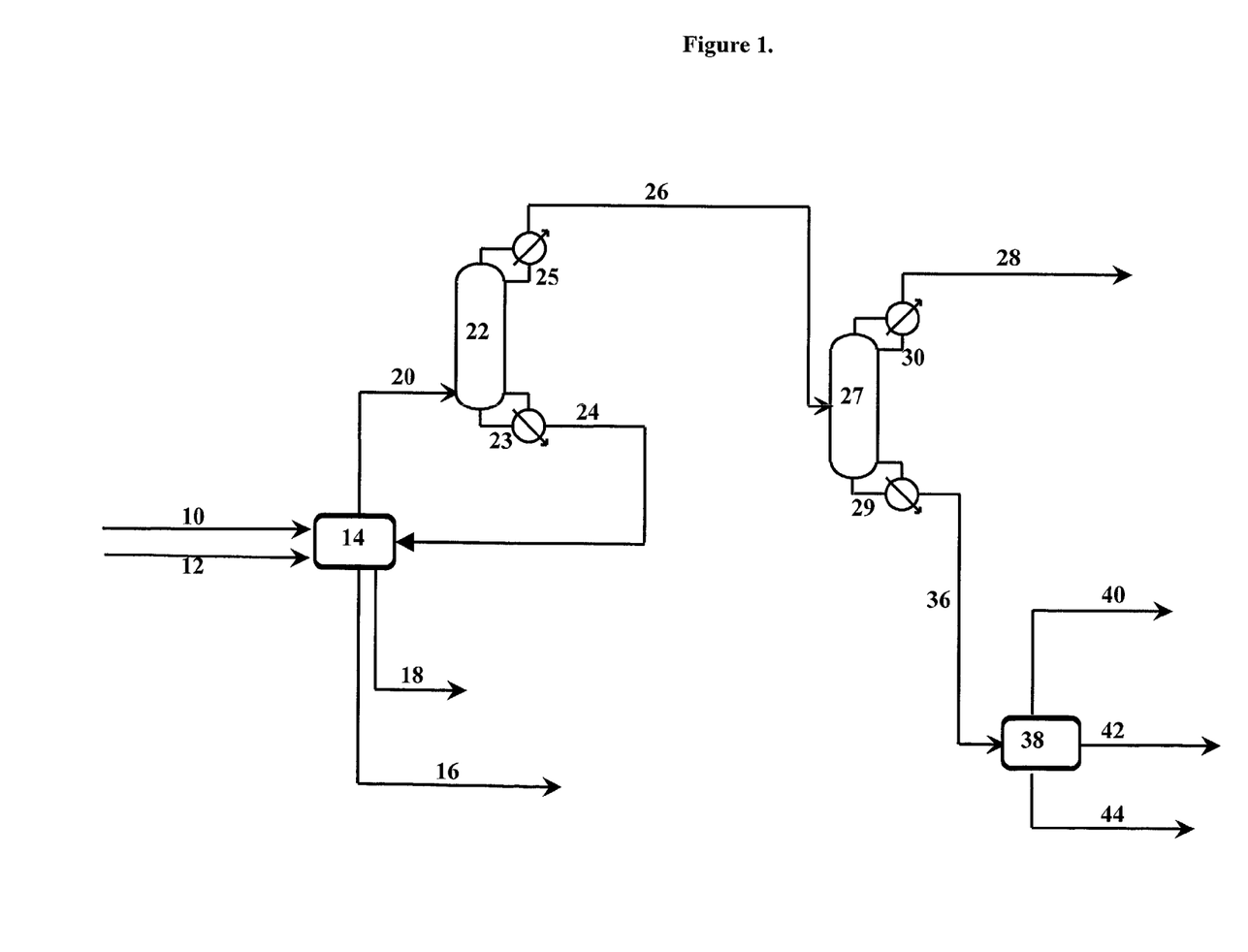
FIG. 1 is a schematic of an embodiment of the present invention.

Certain embodiments of the present invention can be better understood by reference to FIG. 1. The core of the invention comprises the following elements: feed stream (10), azeotroping agent (12), reactor (14), heavy phase of first bottoms stream (16), light phase of first bottoms stream (18), and first vapor stream (20). Additional numbered elements are involved in purification of lactide. Note that the heavy phase of first bottoms stream (16) and the light phase of first bottoms stream (18) exist when the azeotroping agent (12) and the feed stream (10) are immiscible. The bottoms stream can comprise a single phase in certain embodiments when the two are miscible.

A feed stream (10) comprising at least one of a hydroxy organic acid, an ammonium salt of a hydroxy organic acid, an amide of a hydroxy organic acid, or an ester of a hydroxy organic acid that was originally present in the feed stream is fed to reactor (14). The feed stream (10) can further comprise water and impurities (e.g., sugars, alcohols, proteins, cell fragments, other organic acids, amino acids, impurities present in a fermentation medium or impurities produced by a fermenting organism).

Preferably the hydroxy organic acid of the free hydroxy organic acid, of the ammonium salt, of the amide, or of the ester of the hydroxy organic acid has from 2 to 6 carbon atoms. Furthermore, the hydroxy organic acid can be an alpha, beta, delta, gamma, or epsilon hydroxy acid. Glycolic acid and lactic acid are particularly preferred hydroxy organic acids. In certain embodiments in which free lactic acid or an ammonium salt, amide, or ester of lactic acid is a component of the feed stream (10), the lactic acid can be a racemic mixture of optical isomers, or can comprise a majority of one optical isomer, either L- or D-lactic acid. L-lactic acid is a preferred isomer of lactic acid. The feed stream (10) can be a fermentation broth or it can be derived from other sources known in the art. The fermentation stream (10) can be unpurified, concentrated (e.g., dehydrated), acidified, and/or at least partially purified before its introduction into reactor (14). For example, maltose can be removed from a fermentation broth containing low molecular weight organic acids using nanofiltration membranes and/or the fermentation broth can be treated to remove cations using ion exchange or electrodialysis.

Feed streams can comprise esters of a hydroxy organic that are components of the extract (e.g., organic phase of an extraction or reactive extraction) of a fermentation broth or other stream comprising an organic acid (e.g., hydrolyzed polylactide, among others) performed with a liquid extractant. The liquid extractant can comprise an alkylamine in certain embodiments. The alkylamine can for example be trilaurylamine, among others. The liquid extractant can further comprise an extraction enhancer and/or a diluent. Herein an alkylamine is defined as a water-immiscible organic extractant comprising at least one secondary or tertiary amine, in which the aggregate number of carbon atoms is at least 20, or a mixture of two or more such amines. "Diluent" refers to an inert chemical species that can be used as a component of a liquid extractant that comprises an alkylamine for reasons such as to lower the viscosity of the extractant, to increase selectivity of the extractant against other unwanted species, or as a general purpose diluent. This is well known in the art of solvent extraction. A diluent can be a pure or mixed aromatic or aliphatic hydrocarbon. Diluents can be linear or branched chemical species. Examples of diluents that can be used with alkylamine liquid extractants include xylene, toluene, decane, dodecane, kerosene, and mixtures thereof.

"Enhancer" refers to a chemical species that can be a component of a liquid extractant and that acts to enhance the performance of the allkylamine extraction. The enhancer can strengthen the amine:organic acid complex and/or help solubilize the alkylamine:organic acid complex. Use of enhancers in extraction of acids is known in the art. Examples of enhancers that can be used include polar species selected from alcohols, diols, ketones, diketones, fatty acids, chlorinated species, and other species known in the art. Preferably the ratio of the enhancer to the akylamine in the liquid extractant is between about 1:10 and 1:1.

Such extractions and reactive extractions are known in the art. For example, if the organic acid that is to be recovered is lactic acid, the fermentation broth or impure fluid comprising lactic acid can be extracted with dodecane-1,2-diol resulting in extraction and reactive extraction in which at least some the hydroxy organic acid undergoes chemical reaction with the alcohol to produce a mixture of esters in the organic phase, including the dilactic acid ester (e.g. 1,2-dodecanediol-dilactic acid ester) which is recovered in the extract. The extract will typically contain some co-extracted water and it can be further processed such as by methods of dehydration and reaction known in the art to increase the extent of esterification prior to feeding to the azeotropic distillation.

The fermentation broth or fluid comprising organic acid in an ammonium salt, amide or complex that is extracted can be concentrated and/or purified prior to extraction. For example the fermentation broth can be purified using ion exchange chromatography prior to extraction with dodecanol. Thus, the feed stream can comprise an ester of a hydroxy organic acid (such as 1,2-dodecandiol-dilactic acid ester), when the feed stream comprises the amine phase of an extraction performed with a trialkylamine and an alcohol (such as dodecanol), or when the feed stream comprises the back extracted aqueous phase of a trialkylamine-alcohol extraction.

Alternatively, the feed stream can comprise amides produced by reaction of (a) organic acids with ammonia or (b) organic acid esters with ammonia, or by heating of organic acid ammonium salts. Formation of organic acids amides from organic acids in the presence of ammonia is known in the art. Thus, for example, a fermentation broth comprising an ammonium salt of an organic acid can be thermally treated resulting in the formation of amides of the organic acid, and the thermally treated fermentation broth can be used as a feed stream in the present invention. Preferably, the organic acid amide that the feed stream is comprised of is an amide of a hydroxy acid, more preferably it is lactamide. Preferred organic acid amides include lactamide, pyruvamide, beta-hydroxy butyamide, propionamide, and acetamide, among others.

As stated above, the feed stream can be derived from sources other than fermentation. As an alternative to fermentation broth, the feed stream can comprise the products of a digested recycled polymer (e.g., a polyester of an organic acid). Polylactide polymers, polylactic acid polymers, and certain organic polyesters can be treated to produce a feed stream (10) comprising substantial portions of organic acid (e.g. about 30 to 90 wt % of lactic acid or other hydroxy acids). A crude shredded polyester of an organic acid, can be treated with a heated aqueous phase to hydrolyze some or all of the polymer and the resultant stream can then be used as a feed stream (10) for certain embodiments of this invention. The feed stream can comprise organic acids, organic acid ammonium salts, organic acid amides, or mixtures thereof that were derived from the digestion of certain organic polymers.

Preferably the feed stream (10) has less than about 50 ppm of each of the following: sodium, calcium, magnesium, potassium, zinc, manganese, iron, and chromium; more preferably less than about 5 ppm; and most preferably less than about 0.5 ppm. These chemicals can act as racemizing agents, and maintaining the preferred levels in the feed solution can help to reduce racemization of hydroxy acids and/or their cyclic esters In addition to the feed stream (10), azeotroping agent (12) is introduced into the reactor (14). The azeotroping agent (12) can be introduced as a liquid or a vapor. The azeotroping agent (12) is capable of forming an azeotrope with a cyclic ester of a hydroxy organic acid that is to be recovered in the process. In certain embodiments, the azeotroping agent can also form another azeotrope with a hydroxy organic acid present in the feed stream (10). Preferably, the azeotroping agent is a hydrocarbon having a boiling point of between about 100° C. less than and 150° C. more than the boiling point of cyclic ester that is produced from the acid. More preferably, the azeotroping agent has a boiling point of between about 50° C. less than and 50° C. more than the boiling points of the cyclic ester that is produced from the acid. For example, where the cyclic ester of the hydroxy acid is lactide (boiling point 205° C. at 191 mm Hg), preferably the boiling point of the azeotroping agent at 191 mm Hg is between about 105° C. and 355° C., more preferably between about 155° C. and 255° C. The azeotroping agent preferably is a hydrocarbon having from 7 to 16 carbon atoms. The azeotroping agent can be an aromatic or aliphatic hydrocarbon, and if aliphatic, it can be branched, unbranched or cyclic. Diethylbenzene, dodecane, decane, octylbenzene, propylbenzene, ethylbenzene and mixtures thereof, are preferred, and dodecane and diethylbenzene are particularly preferred when L-lactide is to be recovered. In this example, the lactic acid will tend to also form an azeotrope with some agents under the same conditions used to distill the lactide. The azeotroping agent may have oxygen or other polar groups to enhance the separation of the lactic acid—agent azeotropic pair from the lactide—agent azeotropic pair. The azeotroping agent can be, in certain embodiments, an ether, for example an ether having from 7 to 16 carbon atoms. Ethers used as azeotroping agents can be either aliphatic or aromatic. One or a mixture of more than one of these hydrocarbons can be used as the azeotroping agent. Dodecane and diethylbenzene have relatively low toxicity and low reactivity. Temperature and pressure can be lowered to reduce reactions such as reaction of lactide with lactic acid leading to lactide losses, or temperature and pressure can be increased to alter reaction equilibria or rate.

In a contrasting example, gamma-butyrolactone is formed from 4-hydroxybutyric acid. In this case, the azeotrope agent can be selected to favor the removal of the more volatile cyclic ester.

The reactor (14) into which the feed stream (10) and the azeotroping agent (12) are introduced can be a flash reactor or another suitable reactor known in the art. The feed stream (10) and the azeotroping agent (12) are mixed and can be heated further in the reactor (14). Either the feed stream (10) or the azeotroping agent (12) or both can be heated prior to being mixed in the reactor (14). The reactor (14) can alternatively be a suitable wiped film evaporation unit, a falling film evaporation unit, a tray distillation column with pumparounds, a packed column, or other mechanical arrangement suitable for contacting, heating, and mixing.

"Heated in the reactor" should be understood to include heating by a reboiler or other heat exchange device that returns a stream to the reactor. In certain embodiments, "heated in the reactor" can include introducing a hot saturated or superheated vapor stream that contains excess vapor that will condense and supply heat to the system. The mixing (e.g. contacting) of the feed stream (10) and the azeotroping agent (12) in the reactor (14) preferably is performed by countercurrent flow of the two streams. When the feed stream (10) comprises lactic acid and some water and the azeotroping agent (12) is dodecane, the mixture preferably is heated to between about 130° C. and 170° C., while the pressure in the system is maintained at about 190 mm Hg. The pressure can be as high as between about 740 and 780 mm Hg, preferably 760 mm Hg for lactic acid systems and even higher for glycolic acid systems.

Lower pressures can be used, but can require different equipment for implementation. Use of lower pressures in the present invention leads to lower temperatures that can reduce the rate of racemization. In particular, choice of a combination of concentrations, azeotroping agent, and pressure to give temperatures below 180° C. lead to reduced racemization rates. The temperature and pressure in the reactor (14) is sufficient to cause at least some production of the cyclic ester from the hydroxy organic acid and to produce a vapor stream comprising at least one azeotrope that comprises the azeotroping agent and the cyclic ester of the hydroxy organic acid. When the feed stream (10) comprises at least one of an ammonium salt of a hydroxy organic acid, an amide of a hydroxy organic acid, or an ester a hydroxy organic acid, it is preferred that the heating is also sufficient to cause at least some decomposition of the salt, the amide or the ester. However the temperature and pressure is preferably not so high that the rate or extent of racemization of optical isomers of a hydroxy acid present is increased or that high boiling point impurities (such as malic acid) are significantly volatilized.

A first vapor stream (20) comprising the cyclic ester of the organic acid and the azeotroping agent is produced. The first vapor stream (20) can further comprise some water and/or hydroxy organic acid in certain embodiments. Preferred cyclic esters are lactide (particularly L-lactide) and glycolide.

This first vapor stream (20) can then be further purified in a variety of ways. One such way is by partial condensation followed by melt crystallization of the condensate. Another method is immediate condensation (i.e., prior to other process steps) of the first vapor stream (20) and crystallization of the cyclic ester. The first vapor stream (20) can also be purified further by distillation, as shown in FIG. 1, using a first column (22), a second column (27), and a separator (38). In this mode of further purification of the first vapor stream (20), it is introduced into a first column (22). The unvaporized mixture in the reactor (14) can be removed as a first bottoms stream, and when the feed stream (10) and the azeotroping agent are immiscible, separated into two phases: a heavy phase (16) and a light phase (18). The heavy phase (16) can comprise impurities with relatively high boiling points (such as malic acid, glycerol, and glucose), while the light phase (18) comprises primarily azeotroping agent. In the first column (22) further separation is accomplished, yielding a second overhead vapor stream (26) that comprises at least one azeotrope comprising cyclic ester of the hydroxy organic acid. The second overhead stream (26) can further comprise an azeotrope comprising the hydroxy organic acid, and azeotroping agent. The second overhead stream (26) can, for example, comprise as many as three different binary azeotropes: one comprising the cyclic ester of the hydroxy organic acid and the azeotroping agent, another comprising water, and the azeotroping agent, and a third comprising the hydroxy organic acid and the azeotroping agent. The first column bottoms stream (24) from the first column (22) can be recycled back to reactor (14). The bottoms stream (24) will comprise azeotroping agent and at least some impurities such as glycerol and traces of malic acid, for example. Heat can be provided to the liquid in the first column by means of a reboiler (23).

The second overhead vapor stream (26) is fed to a second column (27) that can optionally comprise catalysts. Such catalysts can aid in the production of cyclic esters from hydroxy organic acid present in the second overhead stream (26). For example, an acid catalyst can be present in the top half of the second column (27) which converts lactic acid to oligomers, and a ring closing catalyst can be present in the bottom half of the second column (27) to form lactide. Examples of suitable acid catalysts include cationic ion exchange resins. Examples of suitable ring closing catalysts include tin salts. The second overhead stream (26) is preferably introduced mid-column. Note that the majority of the cyclic ester has already been formed in the reactor or column (14). Additional ring closing can occur in the second column (27) under certain circumstances, but this is not necessary for the invention. If the hydroxy acid is lactic acid, preferably the temperature of the second column (27) is between about 135° C. to 200° C. Heat can be provided to the compounds in the second column (27), for example, by means of a reboiler (29). Reaction and separation in the second column (27) results in a third overhead vapor stream (28) and a final product stream (36). Thus in certain embodiments there can be at least three vapor streams: a first vapor stream (20), a second overhead stream (26), and a third overhead stream (28). Both the first vapor stream (20) and the second overhead stream (26) comprise the majority of the cyclic ester of the hydroxy organic acid, but the first vapor stream (20) is the least pure. The first column (22) acts to increase the purity of the cyclic ester (e.g., lactide) product, and the second column (27) can help to further increase the yield and purity of the product.

Optionally a portion of the third overhead stream (28) can be condensed and recycled (30) to the second column (27). The third overhead stream (28) comprises water (water is produced by the ring closing reaction, and in certain embodiments there can be additional water that was carried over from the first vapor stream (26)) and azeotroping agent, while the final product stream (36) comprises cyclic ester of the hydroxy organic acid and azeotroping agent. The cyclic ester can crystallize and form solid material, but it is desirable to keep the temperature in the second column (27) above the melting point of the solid to prevent operational difficulties. Azeotroping agent can be recovered from the third overhead stream (28) and recycled in the same process or in other processes.

In certain embodiments in which dodecane is used as the azeotroping agent in the process, it is preferred that the cyclic ester of the product stream is washed with a low boiling solvent, such as hexane. Preferably, the cyclic ester recovered in the first product stream is lactide or glycolide, with lactic acid being the hydroxy organic acid that is reacted to produce the former and glycolic acid being reacted to produce the latter. When the cyclic ester that is produced is lactide, it is preferred that it is L-lactide having an optical purity of about 95% or more.

The final product stream (36) can be introduced into washing, drying, crystallization, or other treatments indicated by separator (38) yielding vapor stream (40); liquid stream (42) and solid stream (44). The azeotroping agent and the cyclic ester of the hydroxy acid can be such that they form two separate liquid phases (e.g., when the azeotroping agent and the cyclic ester are immiscible) that can make recovery of the cyclic ester easier. Typically upon cooling the cyclic ester will crystallize and can be filtered and dried and forms a solids stream (44). However, there are many variations possible for the final purification step (38).

The process described above can use vacuum to separate vapor streams. Furthermore, the process can be performed either as a batch or a continuous process. Processes of the present invention can be performed using relatively high pressure equipment (e.g. as much as between about 740 and 780 mm Hg and typically about 190 mm Hg rather than about 10 mm Hg as is used in certain non-azeotropic lactide production processes U.S. Pat. No. 5,142,023).

Furthermore, when processes of the present invention are compared to certain processes known in the art for producing cyclic esters of hydroxy organic acids with optical activity, the present invention can reduce racemization reactions, because the processes of the present invention can be performed at relatively lower temperatures. For example, in a process of the present invention in which a L-lactic acid feed is used with dodecane to produce L-lactide, the formation of lactide/dodecane azeotrope can occur at about 164° C. or less at 190 mm Hg, as compared to a known process for producing lactide without azeotropic distillation (Yamaguchi et al. U.S. Pat. No. 5,502,215), which requires a temperature of about 190° C. It is known in the art that increased temperature can correlate with increased racemization.

Furthermore, in the specific example of lactide/dodecane azeotropic distillation processes, dodecane vapor can simplify heat transfer problems found in lactide formation, and can avoid the need for wiped film distillation units. The use of dodecane can also aid in the removal of water, because water and dodecane form an additional azeotrope that can be distilled from the first vapor stream or the first product stream. Still further, the boiling point difference between the lactic acid/dodecane azeotrope and the lactide/dodecane azeotrope is greater than the difference between the boiling points of lactic acid and lactide, which can enhance the separation of lactic acid and lactide.

As discussed above, the present invention can be used to produce and purify cyclic esters of hydroxy organic acids, or to purify such esters produced via other means. In certain embodiments, a crude composition of a cyclic ester of a hydroxy organic acid is mixed with an azeotroping agent that is capable of forming an azeotrope with the cyclic ester. Preferably, the azeotroping agent is a hydrocarbon having a boiling point of between about 100° C. less than and 150° C. more than the boiling point of the cyclic ester. More preferably, the azeotroping agent has a boiling point of between about 50° C. less than and 50° C. more than the boiling point of the cyclic ester. In other respects, the preferences for the azeotroping agent are as described above. The hydrocarbon is preferably selected from the group consisting of diethylbenzene, dodecane, decane, octylbenzene, propylbenzene, ethylbenzene, and mixtures thereof. Dodecane and diethylbenzene are particularly preferred for the reasons explained above. In addition to cyclic ester of a hydroxy acid, the crude composition of a cyclic ester of this embodiment can comprise such impurities as the hydroxy organic acid from which it was produced. Preferably the crude composition of a cyclic ester comprises glycolide or lactide. In certain embodiments, the crude composition of a cyclic ester further comprises a hydroxy organic acid and the azeotroping agent is unable to form an azeotrope with the hydroxy organic acid. The hydroxy organic acid can be a precursor that can be reacted to from the cyclic ester, but does not have to be a possible precursor.

The mixture is heated to produce a vapor stream that comprises the azeotrope. As described above the heating can be done in a flash reactor. The vapor stream comprising the azeotrope is condensed, and the cyclic ester of the hydroxy organic acid can be recovered. Preferably the azeotroping agent and the cyclic ester of the hydroxy acid are such that they form two separate phases (e.g., two liquid phases or a liquid phase and a solid phase), which can make recovery of the ester easier.

Certain embodiments are directed to a process for the production of at least one cyclic ester of a hydroxy organic acid from a feed stream comprising at least one of a hydroxy organic acid, an ammonium salt of a hydroxy organic acid, an amide of a hydroxy organic acid, or an ester of a hydroxy organic acid. A feed stream is mixed with at least one azeotroping agent, wherein the feed stream comprises a hydroxy organic acid, an ammonium salt of a hydroxy organic acid, an amide of a hydroxy organic acid, or an ester of a hydroxy organic acid and wherein the azeotroping agent is capable of forming at least two azeotropes, a first azeotrope comprising the hydroxy organic acid, and a second azeotrope comprising a cyclic ester of the hydroxy organic acid. The feed stream and the azeotroping agent are as described above. Mixing (e.g. contacting) and heating of the azeotroping agent and the feed stream is performed in a first column to produce a first vapor stream that comprises a first azeotrope comprising a hydroxy organic acid and the azeotroping agent. Heat can be provided by a flash reactor. When the feed stream comprises at least one of an ammonium salt of a hydroxy organic acid, an amide of a hydroxy organic acid, or an ester of a hydroxy organic acid, it is preferred that the heat is also sufficient to cause decomposition of at least some of the salt, amide, or ester. The first vapor stream can further comprise a second azeotrope comprising a cyclic ester of a hydroxy organic acid and the azeotroping agent. The first vapor stream is fed to a second column, where the hydroxy organic acid of the first vapor stream is reacted to produce at least one cyclic ester of the hydroxy acid and water. The first vapor stream can optionally be dehydrated before being fed into the second column. The second column can comprise catalyst for cyclic ester formation. A second overhead vapor stream is obtained from the second column and comprises water and azeotroping agent. Water in the second overhead can be a product of cyclic ester formation in the second column and/or can have been carried over in the first vapor stream. A bottoms stream from the second column comprises at least one cyclic ester of the hydroxy acid. (The first vapor stream and the second overhead stream in this embodiment have different compositions than those described in previous embodiments.)

Another embodiment is directed to a process for the separation of a hydroxy organic acid from a cyclic ester thereof. A feed stream comprising a hydroxy organic acid and a cyclic ester thereof is mixed with at least one azeotroping agent that is capable of forming at least two azeotropes, a first azeotrope comprising the hydroxy organic acid and a second azeotrope comprising a cyclic ester of the hydroxy organic acid. The feed stream and the azeotroping agent are as described above. At least one of the feed stream, the azeotroping agent, or a mixture of the two is heated to produce a first vapor stream that comprises a first azeotrope comprising the hydroxy organic acid and the azeotroping agent. The first vapor stream is separated from the mixture to produce a bottoms stream comprising the cyclic ester of the hydroxy organic acid and the azeotroping agent.

Yet another embodiment is directed to a process for the separation of L-lactide from meso-lactide. A feed stream comprising L-lactide and meso-lactide is mixed with at least one azeotroping agent that is capable of forming at least two azeotropes, a first azeotrope comprising L-lactide, and a second azeotrope comprising meso-lactide. Upon heating of at least one of the feed stream, the azeotroping agent, or the mixture of the two a first vapor stream is produced comprising a first azeotrope comprising the L-lactide and the azeotroping agent. The first vapor stream is separated from the mixture to produce a bottoms stream comprising the meso-lactide and the azeotroping agent.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1 n-Dodecane Azeotropic Compositions Predicted at 191 mm Hg Based on a Group Contribution Method Estimation of Infinite Dilution Activity Coefficients which were in Turn Used to Estimate Binary NRTL (Non-Random Two Liquid) Interaction Parameters

| Species | Azeotrope boiling point at 191 mm Hg | Temperature drop from boiling point of pure component | wt % |
|---|---|---|---|
| Water | 65.11° C. | 0.27° C. | 89.5% water |
| Lactic Acid | 135° C. | 9° C. | 52% Lactic acid |
| Lactide | 162° C. | 43° C. | 19% Lactide |
| Lactoyl-lactic acid | 164° C. | 54° C. | 7% Lactoyl-lactic acid |
| Boiling points of pure components at 191 mm Hg | | | |
| Pure Water | | | 65.38° C. |
| Pure Lactic Acid | | | 144° C. |
| Pure n-Dodecane | | | 165.68° C. |
| Pure Lactide | | | 205° C. |
| Pure Lactoyl-lactic acid | | | 218° C. |

In this simulation there are four azeotropes for the n-dodecane system. It is possible to select other azeotroping agents that are heterogeneous and that favor efficient separation and recovery of lactide in preference to the other species. This involves using one or more other azeotroping agents such as hexadecane, decane, diethylbenzene isomers, and anisole, among others at different pressures and temperatures, based on a selection of the optimum agent for the chosen variation of the invention of heterogeneous azeotropic distillation sequence combined with subsequent separation steps.

EXAMPLE 2

Azeotropic Distillation of Lactide with n-Dodecane

A batch charge of 80 g n-dodecane (106.6 ml, Acros Organics catalog # 11759-5000) and 5 g crystalline meso-lactide (3,6-dimethyl-1,4-dioxane-2,5-dione, Aldrich catalog # 30,314-3) was made to a 250-mL three-neck flask, which was attached to a standard vacuum distillation system via a Claisen adapter and a 5 in Vigreaux column. Both the adapter and column had a vacuum jacket and these as well as the flask and distillation head were wrapped in extra insulation to minimize heat loss. The lactide-dodecane mixture was stirred by means of a magnetic stirrer and Teflon coated stirring bar in the flask. Heating was provided by a 250-mL heating mantle and was controlled by a variable autotransformer (power output 50%). The temperature was measured at four different points by thermocouples: liquid phase (T1), vapor phase above the liquid (T2), mid-column (T3), and column head (T4). Reduced pressure was maintained in the system by a membrane vacuum pump. In order to condense any vapors escaping from the distillation system through the vacuum line, a cold trap immersed into an iso-propanol/dry ice bath (−78° C.) was also applied.

Distillation of the above mixture led to an instant build up of a layer of solid lactide on the walls of the primary (water cooled) condenser, while dodecane and a small amount of lactide were collected in the receiver. The temperature and pressure conditions during distillation were T1=161.8–164.0° C., T2=160.3–162.8° C., T3=155–156° C., T4=148–153° C., and the pressure was at about 190 mm Hg. Distillation was carried out for 16 minutes. The solid lactide product was recovered from the condenser and receiver by dissolving it in a minimum amount of acetonitrile and separating it from dodecane. Some undistilled lactide was recovered in the same way from the reboiler flask after cooling to room temperature. The amount of lactide in these solutions was determined by HPLC analysis using a Waters C18 neutral column and an aqueous mobile phase containing 10% acetonitrile and 0.085% $H_3PO_4$. The acetonitrile solution of lactide was freshly diluted 1:10 in deionized water prior to analysis.

In conclusion, 4.77 g (95.3%) lactide was distilled along with 39.2 g dodecane. This includes all forms of lactide collected in the condensate and condenser. The small scale of the equipment means that lactide is present both as solid and present in the distilled dodecane. This corresponds to a 1:8.2 lactide/dodecane weight ratio, which suggests that the azeotrope contains about 11 wt % lactide. The calculated flow rate of dodecane was 147 g/h.

EXAMPLE 3

Continuous Dodecane Vapor-Stripper Azeotropic Distillation of 50% Lactic Acid n-Dodecane (100 g, Acros Organics catalog # 11759-5000) was placed in a 250-mL three-neck round bottom flask equipped with a magnetic stirrer and connected to a standard vacuum distillation apparatus via a 6 in column. The column was filled with Pro-Pak (Ace Glass, Inc., catalog # 6624-04) stainless steel dump-packing 5.5 inch high. The flask, column, and distillation head were well insulated against heat loss. Vacuum was provided by a membrane vacuum pump. Dodecane was heated to distill by a transformer controlled (46% power output) heating mantle. The temperature was measured by thermocouples at three different points: liquid phase (T1), vapor phase above the liquid (T2), and column head (T3). A 50% lactic acid solution containing 10 impurities to simulate a fermentation broth was continuously fed at the column head. The impurities were as follows: D-glucose (0.81 g/L), L-malic acid (0.10 g/L), D-mannitol (0.59 g/L), succinic acid (0.59 g/L), 2,3-butanediol (1.24 g/L), glycolic acid (0.84 g/L), acetic acid (0.42 g/L), formic acid (0.44 g/L), glycerol (7.31 g/L), pyruvic acid (0.11 g/L).

Distillation resulted in purification of lactic acid, which was collected together with dodecane as a two phase system in the receiver. During this process a colorless crystalline material, e.g. lactide, precipitated in the condenser. Since the condensed aqueous lactic acid was flowing over the solid material, it was continuously washed away and dissolved, which prevented determination of the exact amount of lactide formed. Azeotropic distillation of 6.17 g of 50% lactic acid feed took place in 35 min at 195 mm Hg pressure. The operating temperatures were T1=165.6–166.6° C., T2=164.3–165.0° C., and T3=138.5–144.9° C.

The solid material left in the condenser after distillation of lactic acid had been terminated was recovered by dissolving in 2.23 ml of acetonitrile. This solution was analyzed by HPLC as described in Example 2. The analysis confirmed the identity of lactide, although it was mixed with larger amounts of lactic acid monomer and dimer. The recovered lactide represented only about 0.3% of lactic acid (L1 equivalent) in the feed.

EXAMPLE 4

Continuous Azeotropic Distillation of 88% Lactic Acid with n-Dodecane

A batch charge of 90 g n-dodecane and 10 g of an 88% lactic acid solution containing ten impurities was made to a 250-mL three neck flask, equipped with a magnetic stirrer and connected to a standard vacuum distillation apparatus via a set of two packed columns. Each column was filled 3 inch high with Pro-Pak stainless steel dump-packing (Ace Glass, Inc., catalog # 6624-04). The impurities were as follows: malic acid (2.00 g/L), succinic acid (4.02 g/L), maltose (1.61 g/L), maltodextrin (0.80 g/L), acetic acid (0.10 g/L), formic acid (0.11 g/L), pyruvic acid (0.09 g/L), glucose (15.58 g/L), mannitol (19.88 g/L), glycerol (59.89 g/L). The flask, columns, and distillation head were wrapped in an insulating material to minimize heat loss. Heating was provided by a transformer controlled (66% power) heating mantle. The temperature was measured at four different points by thermocouples: liquid phase (T1), vapor phase above the liquid (T2), mid-column (T3), and column head (T4). Reduced pressure was maintained between about 120 and 190 mm Hg by a membrane vacuum pump. In order to recover any vapors escaping from the distillation system through the vacuum line, a cold trap immersed into an iso-propanol/dry ice bath (−78° C.) was also applied.

As distillation of lactic acid proceeded, a significant amount of a colorless crystalline material deposited on the wall of the water cooled condenser. This material was recovered by dissolving in acetonitrile and was analyzed by HPLC, using a Waters C18 neutral column and an aqueous mobile phase containing 10% acetonitrile and 0.085% $H_3PO_4$. The acetonitrile solution was diluted 1:10 in deionized water prior to injecting to the column. When this chromatogram was compared to that of an authentic lactide solution, it was evident that the major component recovered from the condenser is lactide. The weight concentration ratio of lactide:lactic dimer:lactic monomer was 1.7:1.6:1.0.

EXAMPLE 5

Batch Azeotropic Distillation of 50% Lactic Acid with n-Dodecane

A batch charge of 90 g n-dodecane and 10 g of a 50% lactic acid solution containing ten impurities was made to a 250-mL three neck flask, equipped with a magnetic stirrer and connected to a standard vacuum distillation apparatus via a column containing Pro-Pak stainless steel dump-packing (Ace Glass, Inc., catalog # 6624-04) 3 inch high. Impurities in the lactic acid solution were as follows: malic acid (1.00 g/L), succinic acid (2.02 g/L), maltose (0.90 g/L), maltodextrin (0.43 g/L), acetic acid (0.10 g/L), formic acid (0.11 g/L), pyruvic acid (0.09 g/L), glucose (9.00 g/L), mannitol (27.97 g/L), glycerol (33.14 g/L). The flask, columns, and distillation head were wrapped in an insulating material to minimize heat loss. Heating was provided by a heating mantle controlled by an autotransformer. The temperature was measured at four different points by thermocouples: liquid phase (T1), vapor phase above the liquid (T2), mid-column (T3), and column head (T4). Reduced pressure (190 mm Hg) was maintained in the system by a membrane vacuum pump. In order to recover any vapors escaping from the distillation system through the vacuum line, a cold trap immersed into an iso-propanol/dry ice bath (−78° C.) was also applied.

The system was heated to distill and three overhead samples were collected, which all contained heavy and light phases, but the ratio of these significantly increased in favor of the light phase as the head temperature increased. Temperature conditions when these samples were collected are as follows: (1) T1=157° C., T2=156° C., T3= 84.9° C., T4=55.6° C.; (2) T1=159° C., T2=158° C., T3=152.4° C., T4=138.4° C.; (3) T1=160° C., T2=160° C., T3=155° C., T4=146° C. Towards the end of the experiment a colorless solid material also appeared in the water cooled condenser along with some oily liquid. The weight of this product was not determined but it was dissolved in deionized water an analyzed by HPLC the next day. All samples were analyzed on a Jordi Organic Acid column using an aqueous mobile phase containing 10% acetonitrile and 0.085% $H_3PO_4$.

Analysis showed that the three overhead samples contained mainly lactic acid monomer in an increasing concentration. The weight ratio of the concentration of monomeric and dimeric lactic acid was 14.8:1 in the feed, 8.2:1 in the second overhead sample, 4.2:1 in the third overhead sample and 1.8:1 in the sample containing the solids. Lactide readily hydrolyzes to lactic acid dimer in aqueous solution upon standing for one day at room temperature and the dimer also readily equilibrates with the monomer. Therefore, the increasing ratio of lactic acid dimer in the final samples suggests that it probably formed from lactide and that the colorless solid was mainly lactide.

EXAMPLE 6

Recovery of Lactic Acid from a Feed Solution Comprising Bottoms from a Previous Lactic Acid Azeotropic Distillation using Diethylbenzene as an Azeotroping Agent in a One Day Continuous Process without Reflux A 250-mL three neck flask with a stirrer was charged with 77.1 g of bottoms light and 27.6 g of heavy phases produced from a previous azeotropic distillation of 50% lactic acid with no impurities in water feed. The system pressure initially was between 180–240 mm Hg due to a failed vacuum pump. The system was heated under vacuum until condensate flow just started and then the continuous feeds were started. The overhead vapor was drawn to a condenser and condensate receiver. The typical liquid temperature during the run was 125° C. (T1). The vapor immediately above the liquid was 123° C. (T2). The vapor at the top of the head prior to entering the condenser was 109° C. (T3).

The continuous feeds were made at the following average rates: diethylbenzene 102 g/h and water 8.1 g/L. Six overhead condensate samples were collected. A large amount of pot liquid flashed overhead when a new pump was installed, but the heavy phase was returned to the pot for distillation thereafter. The light phase was not returned to the pot or analyzed. The overhead samples consisted of a light and a heavy phase. The phases were separated and analyzed by HPLC.

About 0.5 mg of tiny white, flaky solids were formed at the interface of the two overhead phases. The solids were difficult to recover and, therefore, were not analyzed. It was suspected that the solids were lactide but could not be confirmed unequivocally.

EXAMPLE 7

Separation of Lactic Acid—Dodecane Azeotrope from Lactide—dodecane Azeotrope

Binary molecular interaction parameters were estimated using methods known in the art. These parameters were used to predict vapor liquid equilibrium for all possible azeotropic binary pairs of the following species: L-lactide, n-dodecane, L-lactic acid, water, acetic acid, glycerol, lactoyl lactic acid, and 2,3-butanediol (mixed isomers). The resultant model was used to predict the performance of a distillation column. Heat was supplied to the reboiler equivalent to 5.75 million BTU/hour. This represents a steam usage of 3.46 lb steam/lb lactide. A feed stream consisted of a vapor containing 1068 lb/hr water, 45724 lb/hr dodecane, 3838 lb/hr lactic acid, 481 lb/hr lactic dimer, and 2001 lb/hr of lactide. Additionally there was 20 lb/hr of acetic acid and 14 lb/hr of 2,3-butanediol. It was assumed that in the column, due to the dilute, dehydrating conditions, any lactic dimer would be converted to lactide and water. No other reactions were assumed due to the relatively low temperature of the column, 131° C. in the condenser and 143° C. in the reboiler. These conditions were maintained at a pressure of 1.547 psia or 80 mm Hg. This is a relatively high pressure compared to typical lactide distillation operations, which operate at 10 to 20 mm Hg pressure, and at higher temperatures.

The resultant product streams predicted from the distillation model, in this case, were a bottoms stream containing only lactide and dodecane, with an overhead stream containing unreacted lactic acid, impurities, excess dodecane, and a moderate amount of lactide. This model suggests that it is possible to separate the lower boiling lactic acid—dodecane azeotrope from the higher boiling lactide—dodecane azeotrope.

EXAMPLE 8

Analysis of Xylene as an Azeotroping Agent

It is known in the art to use xylene in processes for lactide formation. Xylene can be used as a dehydrating agent to remove water and as a solvent for lactide formation. Based on the following example, it appears that xylene could not be used effectively in an azeotropic distillation of lactide.

A batch charge of 5.00 g crystalline L-lactide ((3S-cis)-3,6-dimethyl-1,4-dioxane-2,5-dione, Aldrich, catalog # 36704-4) and 160 g xylene (184.8 mL, Acros Organics, Lot # B0076579) was made into a 250-mL three neck round bottom flask which was connected to a standard vacuum distillation apparatus through a 1"×10" column filled 5.5 inch high with a borosilicate glass helices packing (Aldrich, Inc., catalog # Z41,195-7). The system was connected to a membrane pump via a cold trap (−78° C., dry ice/isopropanol), which maintained a stable vacuum of about 23.6 in Hg. The flask, column, and distillation head were insulated well to prevent heat loss. Heating was provided by a 250 mL heating mantle, controlled by an autotransformer. Stirring was provided by a magnetic stirrer/hotplate and a Teflon coated stirring bar. The temperature was measured by thermocouples in the liquid phase in the reboiler (T1) and in the vapor phase at the head of the distillation column (T2), and was monitored continuously.

When the mixture of lactide and xylene was stirred and heated, a homogeneous solution formed. Upon distillation of this solution a colorless liquid was collected in the receiver. Temperatures T1 and T2 remained constant once the condensate started to flow, being 89.2 and 77° C., respectively. Distillation was carried out for 1 hour. Once the apparatus cooled down sufficiently, lactide started to crystallize from the solution left in the reboiler. The lactide was recovered as fine white crystals after the residual xylene was evaporated. To recover any lactide that might have been distilled, the overhead liquid was washed thoroughly with 20 mL of deionized water. The aqueous phase was separated and analyzed by HPLC using a 300×7.8 mm Aminex HPX-87H (BioRad) ion exclusion column and a 0.00919% $H_2SO_4$ solution as the mobile phase at 0.6 mL/min flow rate at room temperature.

The weight of lactide recovered from the reboiler was found to be 4.99 g (99.8%). Chromatography analysis of the overhead washings suggested that as little as 8 mg lactide was dissolved in the overhead condensate, which is 0.16% of the starting material. The calculated flow rate of xylene was 128 g/h. These results suggest that lactide cannot be distilled azeotropically when xylene is used.

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the methods described herein without departing from the concept, spirit and scope of the invention. More specifically, it will be apparent that certain agents which are both chemically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An azeotropic distillation process for the recovery of at least one cyclic ester of a hydroxy organic acid from a feed stream comprising at least one of a hydroxy organic acid, an ammonium salt of a hydroxy organic acid, an amide of a hydroxy organic acid, or an ester of a hydroxy organic acid, comprising the steps of:

mixing a feed stream and at least one azeotroping agent, thereby producing a mixture, wherein the feed stream comprises at least one of a hydroxy organic acid, an ammonium salt of a hydroxy organic acid, an amide of a hydroxy organic acid, or an ester of a hydroxy organic acid and wherein the at least one azeotroping agent is capable of forming at least one azeotrope comprising a cyclic ester of a hydroxy organic acid; and distilling the mixture by a method comprising the steps of (i) heating the mixture sufficiently to produce a first vapor stream comprising at least one azeotrope comprising the cyclic ester of the hydroxy organic acid and the at least one azeotroping agent; and (ii) separating the first vapor stream from the mixture.

2. The process of claim 1, wherein a first bottoms stream is produced as the first vapor stream is separated from the mixture.

3. The process of claim 1, wherein the at least one azeotroping agent is a vapor or a liquid as it is mixed with the feed stream.

4. The process of claim 3, further comprising mixing a catalyst along with the at least one azeotroping agent and the feed stream.

5. The process of claim 4, wherein the at least one azeotroping agent is a liquid and the catalyst is homogeneous in the feed stream or in the at least one azeotroping agent.

6. The process of claim 4, wherein the at least one azeotroping agent is a liquid and the catalyst is heterogeneous in the feed stream or in the at least one azeotroping agent.

7. The process of claim 4, wherein the at least one azeotroping agent is a vapor and the catalyst is heterogeneous in the at least one azeotroping agent.

8. The process of claim 1, wherein the first vapor stream is separated into a second vapor stream that comprises water and azeotroping agent and a product stream comprising cyclic ester of the hydroxy acid and azeotroping agent.

9. The process of claim 1, further comprising the steps of partially condensing the first vapor stream and melt crystallizing the condensate of the first vapor stream.

10. The process of claim 1, further comprising the steps of immediately condensing the first vapor stream and crystallizing the cyclic ester of the hydroxy organic acid therefrom.

11. The process of claim 1, wherein the feed stream comprises a hydroxy organic acid having from 2 to 6 carbon atoms.

12. The process of claim 1, wherein the feed stream comprises a hydroxy organic acid that is lactic acid and the cyclic ester is lactide.

13. The process of claim 1, wherein the feed stream comprises a hydroxy organic acid that is L-lactic acid and the cyclic ester is L-lactide.

14. The process of claim 1, wherein the feed stream comprises a hydroxy organic acid that is glycolic acid and the cyclic ester is glycolide.

15. The process of claim 1, wherein the feed stream comprises an ester of a hydroxy organic acid that is a diol-diester of the organic acid.

16. The process of claim 15, wherein the diol-diester is 1,2-dodecandiol-dilactic acid ester.

17. The process of claim 15 wherein the feed stream further comprises a liquid extractant that comprises an alkylamine.

18. The process of claim 1, wherein the mixture is heated in a flash reactor.

19. The process of claim 1, wherein the feed stream is a fermentation broth.

20. The process of claim 19, wherein the fermentation broth is dehydrated before the feed stream is mixed with the at least one azeotroping agent.

21. The process of claim 19, wherein the fermentation broth is partially purified before the feed stream is mixed with the at least one azeotroping agent.

22. The process of claim 19, wherein the fermentation broth is acidified before the feed stream is mixed with the at least one azeotroping agent.

23. The process of claim 1, wherein the at least one azeotroping agent is a hydrocarbon having a boiling point of between about 100° C. less than and 150° C. more than the boiling point of the cyclic ester.

24. The process of claim 23, wherein the at least one azeotroping agent has a boiling point of between about 50° C. less than and 50° C. more than the boiling point of the cyclic ester.

25. The process of claim 24, wherein the at least one azeotroping agent is an aromatic ether or an aliphatic ether.

26. The process of claim 23, wherein the at least one azeotroping agent has from 7 to 16 carbon atoms.

27. The process of claim 26, wherein the at least one azeotroping agent is aromatic or aliphatic.

28. The process of claim 27, wherein the at least one azeotroping agent is a branched, unbranched, or cyclic aliphatic hydrocarbon.

29. The process of claim 26, wherein the hydrocarbon is selected from the group consisting of diethylbenzene, dodecane, decane, octylbenzene, propylbenzene, and ethylbenzene, and mixtures thereof.

30. The process of claim 1, wherein the process is a continuous process.

31. The process of claim 1, wherein the process is a batch process.

32. The process of claim 1, wherein the cyclic ester is L-lactide or meso-lactide.

33. The process of claim 1, wherein the mixing step is performed in a failing film evaporator, a wiped film evaporator, a tray column, or a packed column.

34. The process of claim 1, wherein at least part of the process is carried out at a pressure of about 740 mm Hg to 780 mm Hg.

35. The process of claim 1, wherein the feed scream further comprises less than about 50 ppm of sodium, calcium, magnesium, potassium, manganese, iron, and chromium.

36. The process of claim 1, wherein the cyclic ester is produced by an esterification reaction which also produces water as a leaving group.

37. The process of claim 1, wherein the cyclic ester is produced by a transesterification reaction which also produces an alcohol as a leaving group.

38. The process of claim 37, wherein the alcohol is methanol.

39. The process of claim 1, wherein the cyclic ester is produced by a reaction that also produces a dimer or an oligomer of the hydroxy organic acid as a leaving group.

40. The process of claim 1, wherein the cyclic ester is produced by a reaction that also produces ammonia as a leaving group.

41. A process for recovering a cyclic ester of a hydroxy organic acid that has 2–6 carbon atoms from a crude composition of a cyclic ester, comprising the steps of:
    mixing a crude composition of a cyclic ester of a hydroxy organic acid with an azeotroping agent that is capable of forming an azeotrope with the cyclic ester, wherein the azeotroping agent is selected from the group consisting of diethylbenzene, dodecane, decane, octylbenzene, propylbenzene, ethylbenzene, and mixtures thereof;
    azeotropically distilling the mixture to produce a vapor stream that comprises an azeotrope comprising the cyclic ester and the azeotroping agent;
    condensing the vapor stream; and
    recovering the cyclic ester.

42. The process of claim 41, wherein the cyclic ester is selected from glycolide and lactide.

43. The process of claim 41, wherein the crude composition further comprises a hydroxy organic acid and the azeotroping agent is unable to form an azeotrope with the hydroxy organic acid.

44. The process of claim 43, wherein the hydroxy organic acid can be reacted to produce the cyclic ester.

45. The process of claim 41, wherein the azeotroping agent is a hydrocarbon having a boiling point of between about 100° C. less than and 150° C. more than the boiling point of the cyclic ester.

46. The process of claim 45, wherein the azeotroping agent has from 7 to 16 carbon atoms.

47. A process for the production of at least one cyclic ester of a hydroxy organic acid from a feed stream comprising at least one of a hydroxy organic acid, an ammonium salt of a hydroxy acid, an amide of a hydroxy organic acid, or an ester of a hydroxy organic acid, comprising the steps of:
    mixing a feed stream and at least one azeotroping agent, wherein the feed stream comprises at least one of a hydroxy organic acid, an ammonium salt of a hydroxy acid, an amide of a hydroxy organic acid, or an ester of a hydroxy organic acid, and wherein the at least one azeotroping agent is capable of forming at least two azeotropes, a first azeotrope comprising a hydroxy organic acid, and a second azeotrope comprising a cyclic ester of a hydroxy organic acid;

heating the mixture comprising the feed stream and the at least one azeotroping agent in a first column to produce a first vapor stream that comprises a first azeotrope comprising the hydroxy organic acid and the at least one azeotroping agent;

feeding the first vapor stream to a second column; and reacting the hydroxy organic acid of the first vapor stream in the second column to produce at least one cyclic ester of the hydroxy acid and water, wherein a second overhead vapor stream from the second column comprises water and at least one azeotroping agent, and a bottoms stream from the second column comprises at least one cyclic ester of the hydroxy acid.

48. The process of claim 47, wherein the first vapor stream further comprises a second azeotrope comprising a cyclic ester of a hydroxy organic acid and the at least one azeotroping agent.

49. The process of claim 47, wherein the heating is performed by a flash reactor.

50. The process of claim 47, wherein the second column comprises catalysts for cyclic ester formation.

51. The process of claim 47, wherein the first vapor stream is dehydrated before being fed into the second column.

52. A process for the separation of a hydroxy organic acid from a cyclic ester thereof, comprising the steps of:

mixing a feed stream comprising a hydroxy organic acid and a cyclic ester thereof and at least one azeotroping agent, thereby producing a mixture, wherein the at least one azeotroping agent is capable of forming at least two azeotropes, a first azeotrope comprising the hydroxy organic acid and a second azeotrope comprising a cyclic ester of the hydroxy organic acid; and distilling the mixture by a method comprising the steps of (i) heating at least one of the feed stream, the at least one azeotroping agent, or the mixture thereof to produce a first vapor stream that comprises the first azeotrope comprising hydroxy organic acid and azeotroping agent; and (ii) separating the first vapor stream from the mixture, producing a bottoms stream comprising cyclic ester of the hydroxy organic acid and azeotroping agent.

53. A process for the separation of L-lactide from meso-lactide, comprising the steps of:

mixing a feed stream comprising L-lactide and meso-lactide and at least one azeotroping agent, thereby producing a mixture, wherein the at least one azeotroping agent is capable of forming at least two azeotropes, a first azeotrope comprising L-lactide, and a second azeotrope comprising meso-lactide; and distilling the mixture by a method comprising the steps of (i) heating the mixture sufficiently to produce a first vapor stream that comprises a first azeotrope comprising L-lactide and azeotroping agent; and (ii) separating the first vapor stream from the mixture, producing a bottoms stream comprising meso-lactide and azeotroping agent.

* * * * *

UNITED STATES PATENT AND TRADEMARK OFFICE
CERTIFICATE OF CORRECTION

PATENT NO. : 6,984,293 B2
DATED : January 10, 2006
INVENTOR(S) : Michael Charles Milner Cockrem and Istvan Kovacs It is certified that error appears in the above-identified patent and that said Letters Patent is hereby corrected as shown below:

Column 22,
Line 6, delete "failing" and insert -- falling --.
Line 11, delete "scream" and insert -- stream --.

Signed and Sealed this

Second Day of May, 2006

JON W. DUDAS
*Director of the United States Patent and Trademark Office*

UNITED STATES PATENT AND TRADEMARK OFFICE
CERTIFICATE OF CORRECTION

PATENT NO. : 6,984,293 B2 Page 1 of 1
APPLICATION NO. : 09/809534
DATED : January 10, 2006
INVENTOR(S) : Michael Charles Milner Cockrem and Istvan Kovacs It is certified that error appears in the above-identified patent and that said Letters Patent is hereby corrected as shown below:

On the title page item (73), add the assignee information as follows:

-- Assignee: Tate & Lyle Ingredients Americas, Inc.
Decatur, IL (US) --

Signed and Sealed this

Twenty-fourth Day of July, 2007

JON W. DUDAS
*Director of the United States Patent and Trademark Office*